United States Patent [19]

Shichi et al.

[11] Patent Number: 4,843,092

[45] Date of Patent: Jun. 27, 1989

[54] IMMUNOSUPPRESSIVE AGENT

[75] Inventors: Hitoshi Shichi, 4455 Pine Tree Trail, Bloomfield Hills, Mich. 48013; Yoshihito Tanouchi, Troy, Mich.; Yoshio Kamada, Tokyo, Japan

[73] Assignee: Hitoshi Shichi, Bloomfield Hills, Mich.

[21] Appl. No.: 94,679

[22] PCT Filed: Apr. 25, 1986

[86] PCT No.: PCT/JP86/00204

§ 371 Date: Jul. 30, 1987

§ 102(e) Date: Jul. 30, 1987

[51] Int. Cl.[4] ........................................ A61K 31/335

[52] U.S. Cl. .................................. 514/450; 514/885

[58] Field of Search ......................... 424/85; 514/450

[56] References Cited

U.S. PATENT DOCUMENTS

| | | | |
|---|---|---|---|
| 3,743,724 | 7/1973 | Kunio et al. | 424/122 |
| 4,136,619 | 1/1979 | Sakamoto et al. | 514/452 |
| 4,166,865 | 9/1979 | Sakamoto et al. | 514/450 |
| 4,205,081 | 5/1980 | Sakamoto et al. | 514/450 |

FOREIGN PATENT DOCUMENTS

| | | | |
|---|---|---|---|
| 2835936 | 2/1979 | Fed. Rep. of Germany | 514/168 |

OTHER PUBLICATIONS

Journal of Antibiotics 23, 105–106 (1970), Oishi et al.

Jpn. Journal of Ophthalmol, 31 (2) 218–29 (1987), Tanouchi et al.

Immunology, 63(3), 471–5 (1988), Tanouchi et al.

*Primary Examiner*—Douglas W. Robinson
*Assistant Examiner*—Zohreh Fay
*Attorney, Agent, or Firm*—Browdy and Neimark

[57] ABSTRACT

The present invention provides an immunosuppressive agent containing an effective amount of one or more of the macrolide antibiotics of the formula (I):

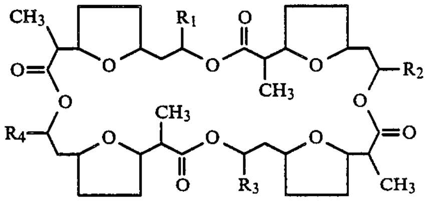

(I)

(wherein each of $R_1$, $R_2$, $R_3$ and $R_4$ is a methyl or ethyl group). The immunisuppressive agent has excellent immuno-suppressive activity and can be employed as an agent for suppressing rejection occurring after organ transplantation and as an agent for treating autoimmune diseases.

4 Claims, 1 Drawing Sheet

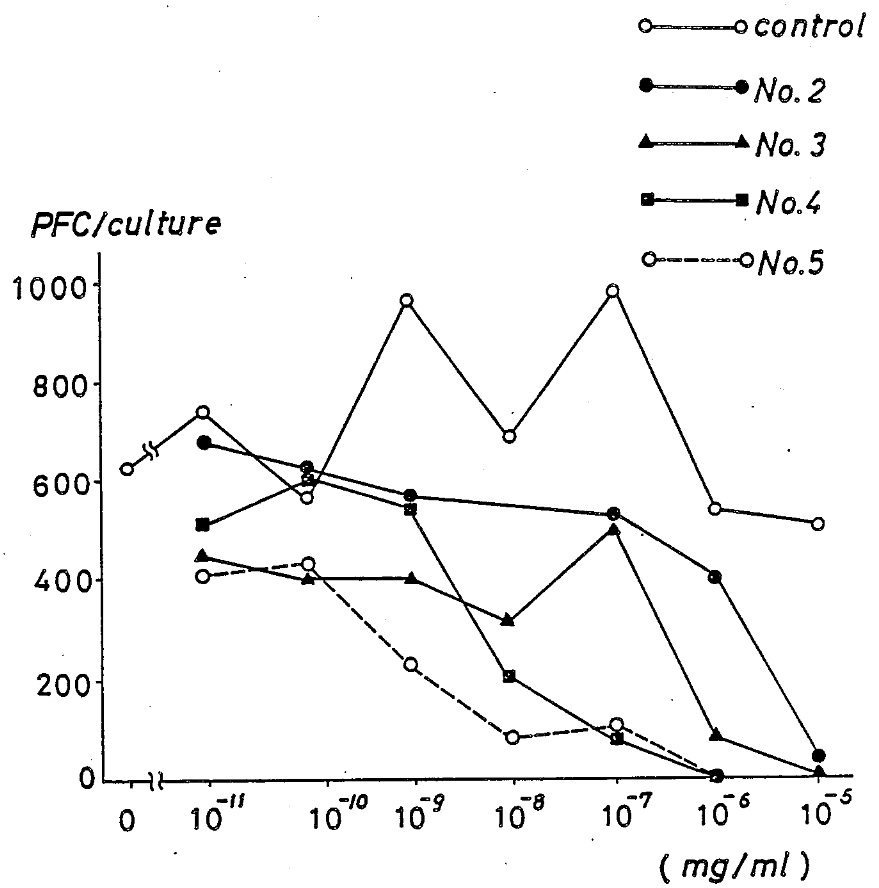
control
No. 2
No. 3
No.4
No.5
PFC/culture
1000
800
600
400
200
0
0
$10^{-11}$
$10^{-10}$
$10^{-9}$
$10^{-8}$
$10^{-7}$
$10^{-6}$
$10^{-5}$
( mg/ml )

IMMUNOSUPPRESSIVE AGENT

The present invention was accomplished with the aid of National Institute of Health, National Eye Institute Grant EY03804.

TECHNICAL FIELD

The present invention relates to an immunosuppressive agent containing an effective amount of one or more of the macrolide antibiotics of the formula (I):

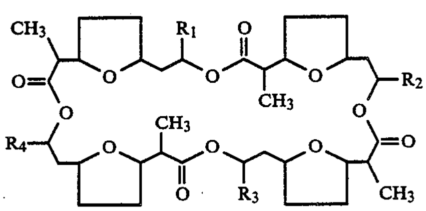

(I)

(wherein each of $R_1$, $R_2$, $R_3$ and $R_4$ is a methyl or ethyl group).

BACKGROUND ART

Macrolide antibiotics of the formula (I) according to the present invention are described in, for example, Helvetica Chemica Acta 38, 1445–1448 (1955), id. 45, 129–138 and 620–630 (1962), Journal of Antibiotics 23, 105–106 (1970), id. 24, 347–352 (1971), etc., and the process for preparing these antibiotics and their physicochemical properties are already known. Further, it is known that these compounds are effective in extermination of vermin such as acarids and cockroaches (see the specification of Japanese Patent Publication No. 46-28100), and it is also known that said macrolide antibiotics are useful as medicines for domestic animals and fowls, more specifically as growth promoting agents for animals (see the specification of Japanese Patent Public Disclosure No. 54-40178) and anti-coccidiosis agents (see the specification of Japanese Patent Public Disclosure No. 53-91143).

As immunosuppressive agents, there are known alkylating agents such as cyclophosamide, nucleic acid antimetabolites such as 6-mercaptopurine and azathiopurine, antibiotics such as mitomycin C, steroids, folic acid antagonists such as methotrexate, and plant alkaloids such as colchicine and vinblastine. These immunosuppressive agents are used as agents for suppressing rejection which may occur after transplantation of human organs or as medicines for treating patients suffering from autoimmune diseases. It has recently been noticed that cyclic polypeptides which are typified by cyclosporin A have immunosuppressive activity and noticeably suppress rejection occurring after organ transplantation. At the same time, vigorous studies have been made to achieve application of cyclic polypeptides to autoimmune diseases, and utility of these polypeptides has been confirmed.

The present inventors made exhaustive studies on the activity of compounds of formula (I) on the immune system which have a cyclic structure similar to that of cyclosporins and, as a result, they found the fact that compounds of the formula (I) have immunosuppressive activity. The present invention is based on this finding.

DISCLOSURE OF THE INVENTION

Compounds of the formula (I) are produced by cultivating *Streotomyces aureus* (FERM-P No. 233), and practical examples are the following five different kinds of compound listed in Table 1 below.

TABLE 1

| | Compound No. | | | | |
|---|---|---|---|---|---|
| | 1 | 2 | 3 | 4 | 5 |
| $R_1$ | $CH_3$ | $C_2H_5$ | $C_2H_5$ | $C_2H_5$ | $C_2H_5$ |
| $R_2$ | $CH_3$ | $CH_3$ | $C_2H_5$ | $C_2H_5$ | $C_2H_5$ |
| $R_3$ | $CH_3$ | $CH_3$ | $CH_3$ | $C_2H_5$ | $C_2H_5$ |
| $R_4$ | $CH_3$ | $CH_3$ | $CH_3$ | $CH_3$ | $C_2H_5$ |
| m.p. (°C.) | 148–149 | 63–64 | 73–74 | 79–80 | 105–106 |

Macrolide antibiotics of the present invention which are obtained by fermentation are mixtures usually containing as principal components about 10% of Compound No. 3, about 40% of Compound No. 4 and about 50% of Compound No. 5, the mixtures being referred to as polynactin complex.

Compounds of the formula (I) are useful as immunosuppressive agents. More specifically, they are employed as agents for suppressing rejection that occurs after organ transplantation and as agents for treating autoimmune diseases. Examples of autoimmune diseases include rheumatoid arthritis, systemic lupus erythematosus (SLE), glomerulonephritis, autoimmune diseases in the ophthalmic region such as uveitis, and autoimmune diseases in the thyroid.

BRIEF DESCRIPTION OF THE DRAWING

FIG. 1 is a graph showing the results of measurement of the anti-SRBC antibody production suppressing effects of selected compounds of the present invention by the PFC method.

BEST MODE FOR CARRYING OUT THE INVENTION

The compounds of the formula (I) may be prepared in the form, for example, of oral or parenteral administration agents by conventional means of formulation. Preferable forms for oral administration include tablets, capsules, granules and liquid preparations.

The dosage of a compound of the formula (I) to human is generally 10–500 mg per day, preferably 50–300 mg per day, although the dosage range slightly differs depending on the method of administration. It is also possible to use two or more different kinds of compound of the present invention in combination.

The compounds of the formula (I) of the present invention show an acute oral toxicity ($LD_{50}$) of 2500 mg/kg or more on mice and rats.

The immunosuppressive effects of the compounds of the formula (I) of the present invention were tested in terms of (1) the anti-SRBC antibody production suppressing effect both in vitro and in vivo and (2) the effect against experimental autoimmune uveitis.

EXPERIMENTAL EXAMPLES (1) Anti-SRBC PFC Test (a) First, $5\times10^5$ sheep red blood cells (SRBC) were added to $2\times10^6$ BALB/C mouse spleen cells suspended in an RPMI-1640 medium (containing 5% of fetal bovine serum), and cultivated for 4 days. Then, the number of cells producing anti-SRBC antibodies was measured by the PFC (plaque-forming cell) method. The results of the measurement are shown in FIG. 1. It should be noted that the compounds of the present invention were added after being dissolved in methanol, and methanol alone was added to the control group. "Nos." given to the compounds in the figure respectively correspond to "Nos." of the compounds shown in Table 1. (The same is the case with Table 2 below).

As will be clear from FIG. 1, all the compounds of the present invention showed strong PFC production suppressing effects.

(b) First, $5\times10^8$ SRBCs were administered intravenously to BALB/C mice (male, 6-week old) for primary sensitization. Then, Compound No. 5 of the present invention, which was suspended in olive oil, was intraperitoneally administered to the mice at the following three different times, that is, immediately after the primary sensitization, 24 hours thereafter, and 48 hours thereafter. Four days after the primary sensitization, spleen cells of the mice were extracted to form single-cell suspensions, and the number of cells producing anti-SRBC antibodies was measured by the PFC method. Olive oil alone was administered to the control group. The results of the measurement are shown in Table 2 below.

TABLE 2

| Compound No. | dosage (mg/kg) | Number of animals | PFC/spleen |
|---|---|---|---|
| Olive oil | — | 12 | 290000 ± 15200 |
| Compound No. 5 | 10 | 6 | 228000 ± 26000[a] |
| | 50 | 6 | 176000 ± 17000[b] |

[a] $P < 0.05$,
[b] $P < 0.001$

As will be clear from Table 2, the compounds of the present invention significantly suppressed PFC production in mouse spleen cells.

(2) Effect against Experimental Autoimmune Uveitis (EAU)

(a) Effect on Development of Uveitis (Method of Experiment)

Experimental animals: Lewis rats (female) each having a weight of about 170 g

Immunization: S antigen extracted and purified from the bovine retina was emulsified in an equivalent of complete Freund's adjuvant (a product available from DIFCO), and 50 μg of this emulsion was injected into the planta pedis of each of the rats.

Tested compounds: Compounds Nos. 3, 4 and 5 shown in Table 1 were mixed together at a ratio of 1:4:5, and the mixture (hereinafter referred to as "PN") was suspended in olive oil using a glass homogenizer to prepare PN samples having various concentrations, which were then injected to the rats. Olive oil alone was injected into rats in the control group.

Administration method: For three groups of rats, 10 mg of PN (in 0.1 ml of olive oil), 20 mg of PN (in 0.2 ml of olive oil) and 30 mg of PN (in 0.3 ml of olive oil) were injected into the femoral muscles of rats, respectively, once a day from the seventh day to the fourteenth day after the immunization. For one group of rats, 10 mg of PN (in 0.1 ml of olive oil) was injected into the femoral muscle of each of the rats once a day from the day of the immunization to the fourteenth day thereafter.

Observation: Development of uveitis was examined by observing the anterior portion of the eye with a slit lamp.

(Results)

Results of observation with a slit lamp are shown in Table 3. As will be clear from Table 3, acute uveitis occurred in 10 to 11 out of 12 eyes of the rats in the control group (injected with S antigen and having no PN administered thereto) at the fifteenth day after the sensitization. For the groups of rats having PN administered thereto from the seventh day after the sensitization, acute uveitis occurred in 4 out of 10 eyes of the rats at a dosage of 10 mg of PN per day, in 6 out of 16 eyes of the rats at a dosage of 20 mg per day, and in only one out of 14 eyes of the rats at a dosage of 30 mg per day. Acute uveitis did not occur in the group of rats to which 10 mg of PN per day had been administered from the day of the sensitization.

TABLE 3

| PN injection (mg/rat/day) | Injection period | Incidence of disease: Control group | Incidence of disease: PN-administered groups |
|---|---|---|---|
| 10 | 7th day–14th day | 11/12 | 4/10 |
| 20 | 7th day–14th day | 10/12 | 6/16 |
| 30 | 7th day–14th day | 10/12 | 1/14 |
| 10 | 0–14th day | 10/12 | 0/8 |

Accordingly, it has been confirmed that the compounds of the present invention are significantly effective against experimental autoimmune uveitis.

(b) Effect on Dermal Test by Secondary Immune Response (Method of Experiment)

Rats were primarily sensitized by the immunization method described in (a). After the sensitization, olive oil alone was injected into the femoral muscles of rats in two control groups, while 20 mg of PN (in 0.2 ml of olive oil) was injected into the femoral muscles of rats in one group once a day from the day of the immunization to the fourteenth day thereafter and also injected into the femoral muscles of rats in another group once a day from the seventh day to the fourteenth day after the immunization. On the fifteenth day after the sensitization, bovine S antigen (100 μg/0.1 ml) was subcutaneously injected into the ventral portion of each of the rats so that they were secondarily sensitized, and the thickness of the skin of each rat was measured with a caliper at each of the times, that is, 3 hours and 24 hours after the secondary sensitization. Two different kinds of control group were prepared for comparison, that is, a control group that was secondarily sensitized (+S antigen) and another control group which was subjected to no secondary sensitization (−S antigen).

(Results)

The results of the skin test are shown in Table 4. As will be understood from Table 4, although there is no significant difference between the control group (+S antigen) and the PN-administered groups in the test carried out when 3 hours had elapsed after the secondary sensitization, the PN-administered groups show lower values than those of the control group (+S antigen) in the test carried out when 24 hours had elapsed after the secondary sensitization.

TABLE 4

| | Control groups: −S antigen | Control groups: +S antigen | PN-administered (20 mg/rat/day) groups: 7th day–14th day | PN-administered (20 mg/rat/day) groups: 0–14th day |
|---|---|---|---|---|
| 3 hours after secondary sensiti- | 3.0 mm | 9.0 mm | 9.0 mm | 9.0 mm |
| | | 8.0 | 8.0 | 8.5 |
| | | 9.0 | 8.0 | 9.5 |

TABLE 4-continued

| | Control groups | | PN-administered (20 mg/rat/day) groups | |
|---|---|---|---|---|
| | −S antigen | +S antigen | 7th day-14th day | 0–14th day |
| zation | | | | |
| 24 hours | 3.0 mm | 9.0 mm | 3.0 mm | 7.0 mm |
| after | | 9.0 | 6.0 | 5.0 |
| secondary | | 8.5 | 6.0 | 5.5 |
| sensiti- | | | | |
| zation | | | | |

Accordingly, it has been confirmed that the compounds of the present invention have an immunosuppressive effect.

FORMULATION EXAMPLE

Sorbitol is dissolved in purified water in an amount which is a quarter of the necessary amount according to the following prescription example. This solution is stirred at a high speed using Polytron® (a product available from KINEMATICA) and while doing so, Compound No. 5 shown in Table 1 and sodium carboxymethyl cellulose are gradually added to the solution and homogenized. Thereafter, the remaining portion of the purified water is added to prepare a suspension. The prepared solution is pipetted into 5-ml brown ampules, sealed and autoclaved at 115° C. for 30 minutes to prepare an injection.

PRESCRIPTION EXAMPLE

| | Concentration (w/v%) |
|---|---|
| Compound No. 5 | 1 |
| Sorbitol | 5 |
| Sodium carboxymethyl cellulose | 2 |
| Purified water | q.s |
| Total amount | 100 |

INDUSTRIAL APPLICABILITY

As has been described above, the compounds of formula (I) of the present invention are useful as immunosuppressive agents and can be employed as agents for suppressing rejection occurring after organ transplantation and as agents for treating autoimmune diseases.

What is claimed is:

1. A method of treating a patient having an autoimmune disease selected from the group consisting of rheumatoid arthritis, systemic lupus erythematosus, glomerulonephritis, autoimmune uveitis, and autoimmune disease in the thyroid, comprising administering to said patient, in order to suppress anti-SBRC antibody production, from about 10 to about 500 mg per day of an antibiotic of the following formula:

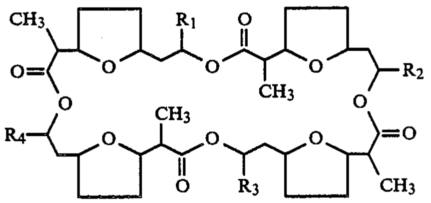

(I)

wherein each of $R_1$, $R_2$, $R_3$, and $R_4$ is selected from the group consisting of methyl and ethyl, in a pharmaceutically acceptable carrier.

2. The method of claim 1 wherein the autoimmune disease is autoimmune uveitis.

3. A method of suppressing anti-SBRC antibody production in a patient comprising administering to said patient from about 10 to about 500 mg per day of an antibiotic of the following formula:

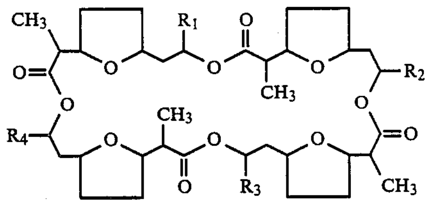

(I)

wherein each of $R_1$, $R_2$, $R_3$, and $R_4$ is selected from the group consisting of methyl and ethyl, in a pharmaceutically acceptable carrier.

4. The method of claim 3 wherein the antibiotic is administered in an amount of from about 50 to about 300 mg per day.

* * * * *